US008252577B2

(12) United States Patent
Kondo et al.

(10) Patent No.: US 8,252,577 B2
(45) Date of Patent: Aug. 28, 2012

(54) MICROORGANISM THAT DISPLAYS BIOTIN ON CELL SURFACE

(75) Inventors: Akihiko Kondo, Kobe (JP); Hideki Fukuda, Kobe (JP); Tsutomu Tanaka, Kobe (JP); Hideo Noda, Amagasaki (JP)

(73) Assignees: Bio-Energy Corporation, Amagasaki (JP); Kansai Chemical Engineering Co., Ltd., Amagasaki (JP)

( * ) Notice: Subject to any disclaimer, the term of this patent is extended or adjusted under 35 U.S.C. 154(b) by 102 days.

(21) Appl. No.: 12/431,102

(22) Filed: Apr. 28, 2009

(65) Prior Publication Data

US 2009/0275110 A1 Nov. 5, 2009

(30) Foreign Application Priority Data

Apr. 30, 2008 (JP) ................................ 2008-118136

(51) Int. Cl.
| | |
|---|---|
| C12N 1/20 | (2006.01) |
| C12N 1/00 | (2006.01) |
| C12N 9/10 | (2006.01) |
| C12Q 1/00 | (2006.01) |
| C12Q 1/48 | (2006.01) |
| G01N 33/567 | (2006.01) |
| G01N 33/53 | (2006.01) |
| C12P 21/06 | (2006.01) |
| C12P 21/04 | (2006.01) |

(52) U.S. Cl. ............ 435/252.3; 435/252.32; 435/252.33; 435/252.9; 435/254.11; 435/255.1; 435/4; 435/7.2; 435/7.5; 435/15; 435/69.1; 435/69.7; 435/193

(58) Field of Classification Search ............... 435/252.3, 435/252.32, 252.33, 252.9, 254.11, 255.1, 435/4, 7.2, 7.5, 15, 69.1, 69.7, 193
See application file for complete search history.

(56) References Cited

U.S. PATENT DOCUMENTS 7,172,877 B2 * 2/2007 Ting ............................ 435/7.72

FOREIGN PATENT DOCUMENTS

| JP | 11290078 A | 10/1999 |
|---|---|---|
| JP | 2002017368 A | 1/2002 |
| JP | 2002176979 A | 6/2002 |
| JP | 2002253267 A | 9/2002 |
| JP | 2003235579 A | 8/2003 |
| JP | 2004049014 A | 2/2004 |
| JP | 2004194559 A | 7/2004 |
| JP | 2004305096 A | 11/2004 |
| JP | 2004305097 A | 11/2004 |
| JP | 2005058010 A | 3/2005 |
| JP | 2005176605 A | 7/2005 |
| JP | 2005245334 A | 9/2005 |
| JP | 2005245335 A | 9/2005 |
| JP | 2005312426 A | 11/2005 |
| JP | 2006136223 A | 6/2006 |
| JP | 2006174767 A | 7/2006 |
| JP | 2006262724 A | 10/2006 |
| JP | 2007020539 A | 2/2007 |
| JP | 2007089506 A | 4/2007 |
| JP | 2007300914 A | 11/2007 |

OTHER PUBLICATIONS

Chen et al., Phage display evolution of a peptide structure substrate for yeast biotin ligase and application to two-color quantum dot labeling of cell surface proteins. J. Am. Chem. Soc., 2007, vol. 129: 6619-6625.*
Parthasarathy et al., An immobilized biotin ligase: Surface display of *Escherichia coli* BirA on *Saccharomyces cerevisiae*. Biotechnol. Prog., 2005, vol. 21: 1627-1631.*
Furukawa et al., Development of novel yeast cell surface display system for homo-oligomeric protein by coexpression of native anchored subunits. Biotechnol. Prog., 2006, vol. 22: 994-997.*
Beckett, Dorothy et al, "A minimal peptide substrate in biotin holoenzyme synthetase-catalyzed biotinylation", Protein Science (1999), vol. 8, pp. 921-929, Cambridge University Press, USA.
Chen, Irwin et al., "Site-specific labeling of cell surface proteins with biophysical probes using biotin ligase", Nature Methods (Feb. 2005), vol. 2, No. 2, pp. 99-104, Nature Publishing Group, USA.
Howard, Peter K. et al., "Nucleotide sequence of the birA gene encoding the biotin operon repressor and biotin holoenzyme synthetase functions of *Escherichia coli*", Gene (1985) vol. 35, pp. 321-331, Elsevier Science Publishers.
Sato, N. et al., "Long anchor using Flo1 protein enhances reactivity of cell surface-displayed glucoamylase to polymer substrates", Appl. Microbiol. Biotechnol. (2002), vol. 60, pp. 469-474, Springer-Verlag.
Matsumoto, Takeshi et al., "Construction of Yeast Strains with High Cell Surface Lipase Activity by Using Novel Display Systems Based on the Flo1p Flocculation Functional Domain", Applied and Environmental Microbiology (Sep. 2002), pp. 4517-4522, vol. 68, No. 9, American Society for Microbiology.
Ueda, Mitsuyoshi et al., "Molecular Breeding of Polysaccharide-Utilizing Yeast Cells by Cell Surface Engineering", Annals New York Academy of Sciences (1998), vol. 864, pp. 528-537.
Murai, Toshiyuki et al., "Assimilation of Cellooligosaccharides by a Cell Surface-Engineered Yeast Expressing Beta-Glucosidase and Carboxymethylcellulase from *Aspergillus aculeatus*", Applied and Environmental Microbiology (Dec. 1998), vol. 64, No. 12, pp. 4857-4861, American Society for Microbiology.

* cited by examiner

*Primary Examiner* — Ganapathirama Raghu
(74) *Attorney, Agent, or Firm* — The Webb Law Firm

(57) ABSTRACT

Provided is a microorganism that can display, on the cell surface, any molecules other than a molecule comprising amino acids, more specifically, a microorganism that displays biotin on a cell surface. The microorganism is capable of co-expressing a biotinylating enzyme and an acceptor peptide having a sequence recognized by the biotinylating enzyme, wherein the acceptor peptide is expressed on the cell surface, so that lysine of the acceptor peptide is biotinylated to display biotin on the cell surface. Also provided is a method for displaying an intended molecule, including not only a molecule comprising amino acids but also any molecules, on a cell surface of a microorganism.

11 Claims, 6 Drawing Sheets

MICROORGANISM THAT DISPLAYS BIOTIN ON CELL SURFACE

BACKGROUND OF THE INVENTION

1. Field of the Invention

The present invention relates to a microorganism that displays a given molecule on the cell surface.

2. Description of the Related Art

Proteins such as enzymes can be displayed on the cell surface of an organism including yeasts by genetically fusing and expressing the protein with an anchor protein, which is capable of anchoring. For various proteins including enzymes, microorganisms that display the protein on the cell surface have been produced (e.g., regarding yeasts, see Japanese Laid-Open Patent Publication Nos. 11-290078, 2002-17368, 2002-176979, 2002-253267, 2003-235579, 2004-49014, 2004-194559, 2004-305096, 2004-305097, 2005-58010, 2005-176605, 2005-245334, 2005-245335, 2005-312426, 2006-136223, 2006-174767, 2006-262724, 2007-20539, 2007-89506, and 2007-300914; and regarding bacteria, see Japanese Laid-Open Patent Publication No. 2005-312426 for *Escherichia coli* (hereinafter, referred to as "*E. coli*"), Japanese Laid-Open Patent Publication No. 2007-89506 for *Corynebacteria*, and Japanese Laid-Open Patent Publication No. 2006-262724 for lactic acid bacteria). When an intended protein is displayed on the cell surface of yeast, the protein can be easily handled. A microorganism that displays an enzyme on the surface can be used as an immobilized enzyme preparation. This microorganism can be nerely incubated to produce an enzyme, and can be recovered after the reaction, and repeatedly used again.

However, displayable molecules have been limited to any molecules that can be produced by organisms, that is, molecules of amino acids (e.g., peptides and proteins) because of the use of only genetic engineering in the cell surface display technique.

SUMMARY OF THE INVENTION

It is an object of the present invention to provide a microorganism that can display a given molecule on the cell surface without limitation of the molecule to molecules comprising amino acids.

The present invention provides a microorganism that displays biotin on a cell surface, wherein the microorganism is capable of co-expressing a biotinylating enzyme and an acceptor peptide having a sequence recognized by the biotinylating enzyme, wherein the acceptor peptide is expressed on the cell surface, so that lysine of the acceptor peptide is biotinylated to display biotin on the cell surface.

In one embodiment, the biotinylating enzyme is *Escherichia coli*-derived biotin ligase, and the sequence recognized by the biotinylating enzyme is the amino acid sequence GLNDIFEAQKIEWHE of SEQ ID NO: 1.

In another embodiment, the microorganism is a yeast or *Escherichia coli*.

The present invention provides a method for displaying an intended molecule on a cell surface of a microorganism, comprising combining the microorganism that displays biotin on a cell surface of the invention, and streptavidin or avidin to which the intended molecule is bound.

The present invention also provides a method for displaying an intended molecule on a cell surface of a microorganism, comprising combining the microorganism that displays biotin on a cell surface of the invention, streptavidin or avidin, and biotin to which the intended molecule is bound.

Further, the present invention provides a method for producing a microorganism that displays an intended molecule on a cell surface, comprising a step of combining the microorganism that displays biotin on a cell surface of the invention, and streptavidin or avidin to which the intended molecule is bound.

The present invention also provides a method for producing a microorganism that displays an intended molecule on a cell surface, comprising combining the microorganism that displays biotin on a cell surface of the invention, streptavidin or avidin, and biotin to which the intended molecule is bound.

Furthermore, the present invention provides a microorganism that displays an intended molecule on a cell surface obtained according to any of the methods above mentioned.

The present invention provides a microorganism that displays biotin, which is a molecule other than any molecules comprising amino acids, on the cell surface. Furthermore, by use of the microorganism that displays biotin on the cell surface, various molecules, including non-natural molecules composed of molecules other than amino acids, can be displayed on the surface of the microorganism.

DESCRIPTION OF THE PREFERRED EMBODIMENTS

Figure 1:
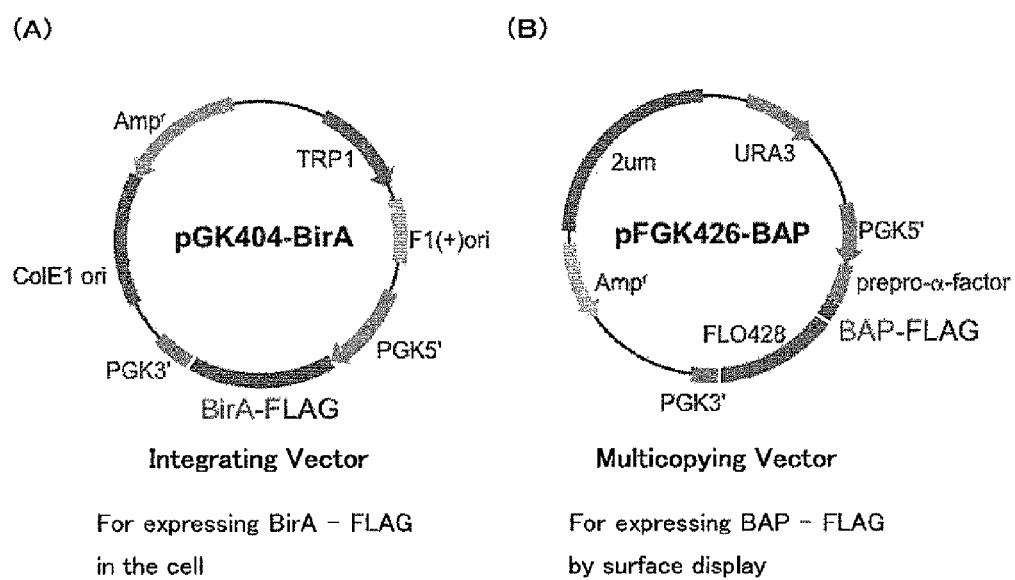
FIG. 1 shows schematic diagrams of (A) a vector for expressing BirA-FLAG in the microorganism cell, and (B) a vector for expressing BAP-FLAG by surface display.

Microorganism that Displays Biotin on the Surface

The present invention provides a microorganism that displays biotin on the cell surface. The microorganism is capable of co-expresses a biotinylating enzyme and an acceptor peptide (also referred to as a "biotin acceptor peptide"; hereinafter, also simply referred to as a "BAP") having a sequence recognized by the biotinylating enzyme (also referred to as a "recognition sequence"). More specifically, according to the microorganism, the biotinylating enzyme can be expressed in the cell of microorganism, or expressed and secreted, and the BAP can be displayed on the cell surface of microorganism. With such a co-expression of the BAP and the biotinylating enzyme, biotin is attached to the BAP by the biotinylating enzyme, and then the BAP to which the biotin is attached is displayed on the cell surface.

The "biotin acceptor peptide" (BAP) refers to a peptide which can be recognized by the biotinylating enzyme to attach biotin to the constituent amino acids. The BAP depends on the biotinylating enzyme, although, for example, when *E. coli* derived biotin ligase (BirA) described later is used as the biotinylating enzyme, the BAP is a peptide of 15 amino acids represented by the recognition sequence GLNDIFEAQKIE-WHE (SEQ ID NO: 1).

The "biotinylating enzyme" refers to an enzyme capable of recognizing the specific sequence (i.e., recognition sequence) of the BAP, and catalyzing the reaction to attach biotin to the constituent amino acid of the BAP. Examples thereof include *E. coli*-derived biotin ligase (BirA). BirA recognizes the recognition sequence of 15 amino acids: GLNDIFEAQKIE-WHE (SEQ ID NO: 1), and catalyzes a reaction of attaching biotin specifically to the side chain of lysine (K) in the recognition sequence in an ATP-dependent manner (*Protein Science*, 1999, 8, 921-929 and *Nature Methods*, 2005, 2, 99-104).

The microorganism of the present invention may be recombinantly engineered to co-express a biotinylating enzyme and a BAP, wherein the BAP is presented on the cell surface. The expression of the biotinylating enzyme may be either expression in the cell, or expressed and secreted. The phrase "recombinantly engineered to co-express a biotinylating enzyme and a BAP, wherein the BAP is presented on the cell surface" refers to that a microorganism that results in both the expression of the biotinylating enzyme and the cell surface display of the BAP is produced by any given genetic engineering procedures. For example, in the case of *E. coli*, which inherently expresses the biotinylating enzyme BirA, genetic engineering procedures need only be performed so as to display the BAP on the cell surface. On the other hand, in the case of biotinylating enzyme-free microorganisms such as yeasts, genetic engineering procedures may be performed to allow the expression of the biotinylating enzyme and the cell surface display of the BAP.

Genes for the biotinylating enzyme and the BAP (i.e., a DNA encoding for the biotinylating enzyme and a DNA encoding for the BAP) can be respectively acquired by preparing primers or probes based on their gene sequence information and executing a method commonly used by those skilled in the art, such as PCR or hybridization. For example, the gene sequence information for BirA is described in *Gene*, 1985, 35, 321-331, and registered as UniProtKB/Swiss-Prot entry P06709, and the gene sequence information for BAP is described in *Protein Science*, 1999, 8, 921-929 and *Nature Methods*, 2005, 2, 99-104. These genes can be used for the introduction into a host cell to produce a microorganism that co-expresses the biotinylating enzyme and the BAP. In order to express an intended gene in the host, an expression cassette further containing a regulatory sequence that regulates the expression of gene (e.g., a promoter and a terminator, and, if necessary, an operator, an enhancer, and the like) may be also constructed. In the case where the biotinylating enzyme is expressed and secreted, the expression cassette further contains a gene sequence encoding for secretion signal sequence as described later. In order to express the BAP, the cell surface display technique as described later in detail may be used.

The term "DNA introduction" refers to the introduction of DNA into a cell for expression. DNA may be introduced using a method, such as transformation, transduction, transfection, cotransfection, electroporation, or the like. Specifically, DNA may be introduced into cells of yeast using, for example, lithium acetate method, protoplast method, or the like. The DNA may be introduced in the form of a plasmid, or may be inserted into the host gene or subjected to homologous recombination with the host gene to be incorporated into chromosomes.

The host may be either yeasts or bacteria (such as *E. coli*, *Corynebacteria*, and lactic acid bacteria). Any microorganism may be used that can display the BAP on the cell surface using the cell surface display technique as described later in detail. Preferable are yeasts and *E. coli*. Also, a microorganism having a selection marker for plasmid expression is preferably used.

There is no particular limitation on the type of yeasts. Examples of the yeasts include those belonging to the genus *Saccharomyces*, the genus *Pichia*, the genus *Kluyveromyces*, the genus *Schizosaccharomyces*, the genus *Zygosacharomyces*, the genus *Yarrowia*, the genus *Candida*, the genus *Hansenula*, and the like. According to the present invention, yeasts belonging to the genus *Saccharomyces* and the genus *Pichia* (e.g., *Saccharomyces cerevisiae*, *Pichia pastris*, etc.) may be preferably used, but there is no limitation to these. In particular, yeasts belonging to the genus *Saccharomyces*, such as *Saccharomyces cerevisiae*, are preferable. It is possible to use any yeast, but flocculating yeasts are preferable in that they can be easily separated after the reaction or in they can be easily immobilized for successive reactions. Alternately, in the case where a flocculation domain is used as a sugar chain-binding protein domain, any yeast can be provided with strong flocculating ability. In the following examples, a *Saccharomyces cerevisiae* YPH499 strain is used, but there is no limitation to this microorganism.

Examples of the bacteria include those belonging to the genus *Escherichia*, the genus *Corynebacterium*, the genus *Lactohacillus*, the genus *Lactococcus*, and the like. According to the present invention, *E. coli*, *Corynebacteria*, lactic acid bacteria, and the like may be preferably used, but there is no limitation to these bacteria. Here, the term "lactic acid bacteria" refers to bacteria that obtain energy by hydrolyzing carbohydrate to produce lactic acid, and encompasses Gram-positive rods, such as microorganisms belonging to the genus *Lactohabillus*, and Gram-positive cocci, such as microorganisms belonging to the genus *Streptococcus*, the genus *Pediococcus*, the genus *Lactococcus*, and the genus *Leuconostoc*. For example, *Lactococcus lactis* IL1403, *Lactobacillus* plantarum WCFS1, *Lactohacillus acidophilus* NCFM, and the like are commercially available and commonly used in the field of fermentation or genetic engineering, and these lactic acid bacteria may be preferably used also according to the present invention. *E. coli* may be preferably used due to readiness in the handling for genetic recombination. There is no particular limitation on the type of *E. coli* as the host, but it is preferably a non-pathogenic strain, and more preferably a commercially available strain commonly used in the field of genetic engineering. Examples thereof include *E. coli* strains K-12, HB101, C600, JM109, DH5α, DH10B, XL-1BlueMRF", and TOP10F. In the following examples, *E. coli* novablue is used, but there is no limitation to this microorganism.

Hereinafter, a technique for displaying the BAP on the cell surface will be described. In order to make the cell surface display of the BAP, for example, for yeasts, (a) GPI anchor attachment recognition signal sequence of cell surface localized protein or (b) sugar chain-binding protein domain of cell surface localized protein may be used (Japanese Laid-Open Patent Publication Nos. 11-290078, 2002-17368, 2002-176979, 2002-253267, 2003-235579, 2004-49014, 2004-194559, 2004-305096, 2004-305097, 2005-58010, 2005-176605, 2005-245334, 2005-245335, 2005-312426, 2006-136223, 2006-174767, 2006-262724, 2007-20539, 2007-

89506, and 2007-300914). For bacteria (such as, *E. coli, Corynebacteria*, and lactic acid bacteria), part of an outer membrane localized protein may be used. For example, a poly-γ-glutamic acid biosynthetic enzyme, PgsA, which is a protein that is localized on the cell surface, and its C-distal end side can be fused to an intended protein at the C terminus to make the cell surface display of the intended protein (Japanese Laid-Open Patent Publication Nos. 2005-312426, 2007-89506, and 2006-262724). A gene fragment is prepared in which a gene encoding for a protein desired to be expressed on the cell surface is fused to the 3' end of the fragment of PgsA encoding gene, which contains at least the anchor portion of the first to 150th nucleotides from the 5' end, and the fusion is inserted into an appropriate plasmid, and a bacterium is transformed therewith, to provide a C terminal cell surface display bacterium. Herein, proteins for making the cell surface display are also collectively referred to simply as "anchor proteins".

Examples of the cell surface localized protein that can be used for yeasts include sex-directed flocculation proteins of yeasts, such as α- or a-agglutinin (used as a GPI anchor), FLO1 proteins (FLO1 proteins may be used as a GPI anchor with varying changing the amino acid length at the N terminus: for example, FLO42, FLO102, FLO146, FLO318, FLO428, and the like; *Appl. Microbiol. Biotech.*, vol. 60, pp. 469-474, 2002: "FLO1326" refers to a full length FLO1 protein), FLO proteins (FLOshort or FLOlong, which lacks a GPI anchoring function but use flocculation; *Appl. Environ. Microhiol.*, pp. 4517-4522, 2002), and periplasm localized proteins, such as invertase (not using a GPI anchor).

First, (a) a GPI anchor attachment recognition signal sequence of a cell surface localized protein will be described. A gene that encodes a protein localized on the cell surface by a GPI anchor has genes that respectively encode a secretion signal sequence, a cell surface localized protein (sugar chain-binding protein domain), and a GPI anchor attachment recognition signal sequence, sequentially from the N terminus. The cell surface localized protein (sugar chain-binding protein) is expressed by this gene inside the cell and directed to the outside of the cell membrane by the secretion signal sequence In this regard, the GPI anchor attachment recognition signal sequence is linked via the selectively-truncated C-terminal portion to the GPI anchor of the cell membrane, and anchored at the cell membrane, and subsequently digested with PI-PLC in the vicinity of the base of the GPI anchor, integrated into the cell wall, and anchored at the cell surface, to yield the cell surface display.

Herein, the "secretion signal sequence" refers to an amino acid sequence rich in largely hydrophobic amino acids, that is linked at the N-terminus of a protein (secretory protein) typically to be secreted to the outside of the cell (also including periplasm), and is usually removed when the secretory protein is secreted from the inside of the cell across the cell membrane to the outside of the cell. Any secretion signal sequences capable of directing the expressed product to the cell membrane can be used, with no limitation on the origin of the secretion signal sequence. Preferable examples of the secretion signal sequence include secretion signal sequence of glucoamylase and signal sequence of α- or a-agglutinin of yeast, and the secretion signal sequence of the expressed product own. A part or whole of the secretion signal sequence and pro-sequence may remain at the N-terminus of the protein fused to the cell surface-binding protein without affecting the activities of the fused protein.

Herein, the "GPI anchor" refers to a glycolipid mainly comprising ethanolamine phosphate-6-mannose-α1-2-mannose -α1-6-mannose-α1-4-glucosamine-α1-6-inositol phospholipid, called glycosylphosphatidylinositol (GPI), and the "PI-PLC" refers to phosphatidylinositol-dependent phospholipase C.

The "GPI anchor attachment recognition signal sequence" refers to a specific sequence in the cell surface localized protein, which is recognized by GPI anchor when the GPI anchor is attached to the cell surface localized protein. The GPI anchor attachment recognition signal sequence is generally located at or in the vicinity of the C terminus of the cell surface localized protein. Preferable examples of the GPI anchor attachment recognition signal sequence include a sequence of the C terminal portion of the α-agglutinin of yeast. The GPI anchor attachment recognition signal sequence is in the C terminal portion of a sequence of 320 amino acids from the C terminus of α-agglutinin. Thus, it is particularly useful to use a DNA sequence encoding for a sequence of 320 amino acids from the C terminus.

Accordingly, for example, in the DNA sequence of "the DNA encoding for the secretion signal sequence—the structural gene encoding for the cell surface localized protein—the DNA encoding for the GPI anchor attachment recognition signal", the whole or part of the sequence of the structural gene encoding for the cell surface localized protein can be replaced by the DNA sequence encoding for the BAP in order to prepare a recombinant DNA for the cell surface display of the BAP via the GPI anchor. In the case where the cell surface localized protein is α-agglutinin, it is preferable that in such a recombinant DNA, the replacement by the DNA sequence encoding for the BAP have been made with retaining a sequence encoding for the sequence of 320 amino acids from the C terminus of α-agglutinin. By introducing such a recombinant DNA into yeast for expression, the intended protein is anchored at the cell surface via its C terminus, and thus is displayed on the cell surface.

Next, (b) a sugar chain-binding protein domain of a cell surface localized protein will be described. The "Sugar chain-binding protein domain" refers to a domain that has a plurality of sugar chains capable of interacting or intertwining with sugar chains residing in wall of cell so as to stay on the surface of the cell. Examples thereof include sugar chain-binding sites of lectin, lectin-like protein, and the like, typically including flocculation domains of GPI anchor proteins and flocculation domains of FLO proteins. The "Flocculation domain" of the GPI anchor protein refers to a domain that is located N to the GPI anchoring domain, has a plurality of sugar chains, and is possibly involved in flocculation. The sugar chain-binding protein domain is located downstream to the secretion signal sequence. The secretion signal sequence is as described above.

The sugar chain-binding protein domain of cell surface localized protein (or flocculation domain) is linked to an intendedly expressed peptide so as to display the intendedly expressed peptide on the cell surface. The intendedly expressed peptide can be linked either to the N or C terminus of the sugar chain-binding protein domain (or flocculation domain). According to the present invention, in order to obtain an alternative recombinant DNA for the cell surface display of the BAP, the following sequence may be prepared: (1) the DNA encoding for the secretion signal sequence—the gene encoding for the BAP—the structural gene encoding for the sugar chain-binding protein domain (or flocculation domain); or (2) the DNA encoding for the secretion signal sequence—the structural gene encoding for sugar chain-binding protein domain (or flocculation domain)—the gene encoding for the BAP. In the case where the flocculation domain is used, since the GPI anchor should not be involved in the cell surface display, the DNA sequence encoding for the GPI anchor attachment recognition signal sequence may be only in part present in, or may be absent from the recombinant DNA. Also, it is very useful to use the flocculation domain, in that the length of domain can be easily adjusted (e.g., either FLOshort or FLOlong can be selected) to make the cell surface display of BAP with a more appropriate length, and in that it can be linked to either the N or C terminus of the BAP.

The BAP may be linked directly or via a linker to an element such as an anchor protein. The linker can be designed and prepared as appropriate by those skilled in the art.

The synthesis or linkage (ligation) of the DNAs of the base sequences as explained above can be made using the technique commonly used by those skilled in the art. The linkage (ligation) can be made with appropriate restriction enzymes, linkers, or the like.

Vectors may be produced in the form of a plasmid for expressing the biotinylating enzyme and expressing the BAP on the cell surface, respectively. It is preferable to use a shuttle vector for E. coli and yeast due to facilitating the integration of the DNA. It is more preferable for the starting material for producing the vector to contain, for example, the replication origins of 2 μm plasmid for yeast (Ori) and of ColE1, selection markers for yeast (including drug tolerance genes and auxotrophic marker genes (e.g., genes encoding for imidazoleglycerol-phosphate dehydrogenase (HIS3), beta-isopropyl-malate dehydrogenase (LEU2), tryptophan synthase (TRP5), argininosuccinate lyase (ARG4), N-(5'-phosphoribosyl) anthranilate isomerase (TRP1), histidinol dehydrogenase (HIS4), orotidine-5-phosphate decarboxylase (URA3), dihydroorotate dehydrogenase (URA1), galactokinase (GAL1), alpha-aminoadipate reductase (LYS2), etc.)) and for E. coli (including drug tolerance genes, etc.). In order to express the intended structural gene, it is desirable that the vector also contains so-called regulatory sequences, such as an operator, a promoter, a terminator, and an enhancer, which regulate expression of this gene. Examples thereof include a promoter and a terminator of glyceraldehyde 3'-phosphate dehydrogenase (GAPDH), a promoter and a terminator of phosphoglycerate kinase (PGK), and the like. Examples of plasmids of the starting materials above mentioned include plasmid pYGA2270 or pYE22m containing a GAPDH (glyceraldehyde 3'-phosphate dehydrogenase) promoter sequence and a GAPDH terminator sequence, plasmid pWI3 containing a UPR-ICL (an upstream region of isocitrate lyase) sequence and a Term-ICL (a terminator region of isocitrate lyase) sequence, plasmid pGK404 containing PGK promoter and terminator sequences, and the like.

For example, the DNA encoding for the intendedly expressed product such as BirA or BAP can be inserted between the GAPDH promoter sequence and the GAPDH terminator sequence of the plasmid pYGA2270 or pYE22m, or between the UPR-ICL sequence and the Term-ICL sequence of the plasmid pWI3, or between PGK promoter and terminator sequences of plasmid pGK404, to yield a plasmid vector for use in the introduction into the yeast.

A plasmid vector pCAS is preferably used as a cassette vector for yeast cell surface display, which is obtained by ligating with a vector pGA11 (Ueda et al., *Ann. NY. Acad. Sci.,* 1998, vol. 864, pp. 528-537), a fragment derived from vector pICAS1 (Murai et al., *Appl. Environ. Microbiol.,* 1998, vol. 64, pp. 4857-4861) (which contains a sequence encoding for the secretion signal sequence of glucoamylase gene; a multicloning site that can be recognized by restriction enzymes SacIi, BglII, NcoI, and XhoI; and a sequence encoding for 320 amino acids from the C terminus of α-agglutinin).

As a vector for surface display, pFGK426 is also preferably used. This vector is constructed based on plasmid pGK404, by inserting sequences encoding for yeast-derived α factor gene secretion signal sequence and FLO428 flocculation domain sequence between the PGK promoter and the PGK terminator therein so that they are arranged in the specified order.

In order to construct a vector for displaying biotin on the surface of E. coli, pHLA (Japanese Laid-Open Patent Publication No. 2005-312426) and the like may be used. As a vector for display on the surface of E. coli, it is possible to use a vector containing a constitutively expressable promoter in E. coli and a gene encoding for poly-γ-glutamic acid biosynthetic enzyme PgsA as an anchor protein. pHLA is a vector which contains an E. coli high-level constitutive expression (HCE) promoter sequence (derived from *Geobacillus toebii,* of which sequence is described in Japanese Laid-Open Patent Publication No. 2007-89506) and PgsA gene (full length, including a signal sequence). A vector can be constructed such that the BAP encoding gene sequence is linked downstream to the PgsA gene segment in the PHLA and the linkage is arranged between the signal sequence downstream to the HCE promoter, and the terminator, in the pHLA, and be then transformed into E. coli, to yield the E. coli cell surface dosplay of biotin.

In order to confirm, for the host cell into which the plasmid has been introduced, the expression of the introduced intended gene (e.g., BirA) or the anchoring on the cell surface (e.g., BAP), a tag (such as FLAG tag) may be allowed to be expressed. Such a tag may be linked downstream to the base sequence of the desired structural gene via a linker. Such a linker can be designed based on the procedure commonly used by those skilled in the art. Alternately, a primer may be designed so that the tag is linked downstream to the base sequence of the desired structural gene, and used with PCR to prepare a linkage product of the tag and the desired structural gene.

The microorganism into which the DNA has been introduced may be selected using a selection marker (including drug tolerance genes and auxotrophic marker genes (as described above)). In the case of that a sequence encoding for a tag (such as FLAG tag) has been inserted into a plasmid in advance as described above, an immune antibody method may be employed using an anti-tag antibody (and optionally a fluorescent labeled antibody) to confirm the expressed protein from the intended gene or the cell surface anchored protein from the intended gene. Also, the cell surface display of biotin can be confirmed based on the biotin-streptavidin interaction by acting a fluorescent labeled streptavidin and the cell and determining the fluorescence on the cell surface.

The recombinant microorganism of the present invention can be hypothermically preserved or cryopreserved in a suspension containing a medium that can maintain this microorganism, or may be preserved with hypothermic drying or freeze drying.

The recombinant microorganism of the present invention may be immobilized to a carrier. Herein, the "carrier" refers to any material capable of immobilize a microorganism, and preferably insoluble in water or specific solvents. Preferable examples of the carrier material which can be used according to the present invention include foams or resins, such as polyvinyl alcohol, polyurethane foam, polystyrene foam, polyacrylamide, porous polyvinyl formal resin material, silicon foam, porous cellulose material, and the like. It is preferable to use a porous carrier because dead microorganisms or microorganisms whose growth or activities are reduced can fall off The pore size of the porous material varies depending on the microorganisms and the like, but it is preferably such a size that the microorganisms can sufficiently enter and grow in. The size of 50 μm to 1000 μm is preferabe, but there is no limitation thereto.

Display of the Intended Molecule on the Cell Surface of the Microorganism

Biotin exerts a highly strong interaction with streptavidin or avidin. Accordingly, the present invention provides a method for displaying an intended molecule on a cell surface by use of a microorganism that displays biotin on the cell surface with the interaction of biotin and streptavidin or avidin. The microorganism that displays biotin on the cell surface allows even non-natural molecules, which cannot be produced by genetic engineering, to be displayed on the cell surface.

The present invention provides a method for displaying an intended molecule on a cell surface of a microorganism, which includes combining a microorganism that displays biotin on the cell surface and streptavidin or avidin to which the intended molecule is bound. According to the combining of the method, biotin displayed on the surface of the microorganism is bound to streptavidin or avidin bound to the intended molecule. The combining may be performed by that biotin displayed on the surface of the microorganism is added to streptavidin or avidin to which the intended molecule is bound, or vice versa. Since biotin exerts a highly strong interaction with streptavidin or avidin, the intended molecule can be displayed on the cell surface of the microprganism by binding streptavidin or avidin modified with the intended molecule (or bound by the intended molecule) to biotin which is displayed on the cell surface.

The present invention provides an alternative method for displaying an intended molecule on a cell surface of a microorganism, which includes combining a microorganism that displays biotin on the cell surface, streptavidin or avidin, and biotin to which the intended molecule is bound. According to the combining of the alternative method, biotin displayed on the surface of the microorganism is bound to streptavidin or avidin, which is bound to biotin to which the intended molecule is bound. The combining may be performed by means of any of the followings; i) To a microorganism that displays biotin on the cell surface, streptavidin or avidin, and then biotin to which the intended molecule is bound are added for sequential reactions; ii) To biotin to which the intended molecule is bound, streptavidin or avidin, and then a microorganism that displays biotin on the cell surface are added for sequential reactions; iii) To streptavidin or avidin, a microorganism that displays biotin on the cell surface, and then biotin to which the intended molecule is bound are added for sequential reactions, or vice versa; or iv) a microorganism that displays biotin on the cell surface, streptavidin or avidin, and biotin to which the intended molecule is bound are mixed together. Since streptavidin or avidin has four biotin-binding sites, the intended molecule can be also displayed on the cell surface of the microorganism so as to sandwich streptavidin or avidin (i.e., intended molecule—biotin—streptavidin or avidin—biotin displayed on the cell surface). Also, since streptavidin or avidin has biotin-binding sites other than bound to biotin displayed on the cell surface, it is possible to display a plurality of (up to three) intended molecules (same or different types) on the cell surface.

As the intended molecule, any molecule may be used as long as it can interact with (or can be bound to) biotin, or streptavidin or avidin. Examples of the intended molecule include non-natural molecules, including fluorescent molecules (e.g., fluorescein isocyanate (FITC)), environment-responsive, non-natural molecules (such as molecules of which structure is variable in response to light (e.g., N-isopropyl acrylamide (NIPAM))), ligands with strong affinity to heavy metals (e.g., nickel-specific binding molecules (e.g., nitrilotriacetic acid (NTA) resin)), and non-proteineous catalysts (such as metal catalysts (e.g., titanium dioxide)). Also, examples of the intended molecule include proteins which may be genetically fused to an anchor protein for cell surface display to allow the expression to be prevented or disabled, and proteins that can be biotinylated by chemical modification in vitro but difficult to express by recombination.

According to the microorganism that displays biotin on the cell surface, biotin can be displayed on the cell surface simply by incubating the microorganism. Accordingly, the display of an intended molecule on the cell surface of the microorganism can be made by incubating the microorganism that displays biotin on the cell surface of the microorganism, together with streptavidin to which the intended molecule is bound, or alternatively, biotin to which the intended molecule is bound and streptavidin. The incubating conditions (such as, temperature, pH, and period for incubation) may vary depending on the type of intended molecule or the growth conditions of the microorganism, but any conditions may be applied as long as the microorganism can be appropriately grown, the streptavidin-biotin interaction (or binding) can be obtained without prevention, and the binding of the intended molecule to biotin or streptavidin is not disassociated. In the case where the intended molecule is a protein, conditions may be applied such that the activity of the protein is not significantly reduced.

Furthermore, the present invention provides a method for producing a microorganism that displays an intended molecule on a cell surface, which includes combining a microorganism that displays biotin on the cell surface and streptavidin or avidin to which the intended molecule is bound. According to the combining, biotin displayed on the surface of the microorganism is bound to streptavidin or avidin to which the intended molecule is bound, thereby yielding a microorganism that displays the intended molecule on the cell surface. The present invention provides an alternative method for producing a microorganism that displays an intended molecule on a cell surface, which includes combining a microorganism that displays biotin on the cell surface, streptavidin or avidin, and biotin to which the intended molecule is bound. According to the combining, biotin displayed on the surface of the microorganism is bound to streptavidin or avidin, which is bound to biotin to which the intended molecule is bound, thereby yielding a microorganism that displays the intended molecule on the cell surface. The combinings of the two methods for producing a microorganism that displays an intended molecule on a cell surface may be performed as explained above about those of the two methods for displaying an intended molecule on a cell surface of a microorganism, respectively.

A microorganism that displays the intended molecule on the cell surface, which is obtainable according to any methods mentioned above, is also encompassed by the scope of the present invention.

Hereinafter, the present invention will be described by way of examples, but there is no limitation to these examples.

EXAMPLES

Example 1

Preparation of Yeast that Expresses BirA in the Cell and Displays Biotinylate Peptide on the Cell Surface In order to obtain yeast that expresses BirA in the cell and displays biotinylated peptide on the surface, the following procedure was conducted. First, a vector for expressing BirA (*E. coli*-derived biotin ligase) in the yeast cell was constructed. A PCR was performed with the Forward primer of SEQ ID NO: 2 and the Reverse primer of SEQ ID NO: 3 and *E. coli* genome as a template to amplify a linkage product of BirA gene and FLAG encoding segment. Based on a pRS406 plasmid (obtained from Stratagene), a plasmid pGK404 was prepared that had the replication origins of 2 μm plasmid for yeast (Ori) and of ColE1, TRP1 as selection marker for yeast, and ampicillin tolerance gene as selection marker for *E coli*, and that could be expressed from the PGK promoter. This plasmid pGK404 and the linkage product of BirA gene and FLAG encoding segment were digested with both of NheI and BglII, respectively, followed by ligation. FIG. 1(A) shows a schematic diagram of the final product vector pGK404-BirA, which is an integrating vector for expressing BirA-FLAG in the cell. The vector pGK404-BirA was digested with EcoRV, and then transformed into *Saccharomyces cerevisiae* YPH499 strain using the lithium acetate method.

Next, a plasmid vector for expressing the BAP on the cell surface was constructed in the following manner. A PCR was performed for the extention with the Forward primer of SEQ ID NO: 4 and the Reverse primer of SEQ ID NO: 5 without a template to yield a linkage product of BAP encoding gene and FLAG encoding segment. The linkage product was ligated into a vector pFGK426 for surface display, which had been digested with PacI and SalI, to yield pFGK42G-BAP. FIG. 1(B) shows a schematic diagram of the finally product vector pFGK42G-BAP, which is a multicopying vector for expressing BAP-FLAG by surface display. This vector was used to further transform the strain which had been transformed so as to express BirA as mentioned above.

Comparative Examples 1 and 2

For the sake of comparison, yeast transformed with only pGK404-BirA (Comparative Example 1) and yeast transformed with only pFGK426-BAP (Comparative Example 2) were also prepared.

Example 2

Figure 2:
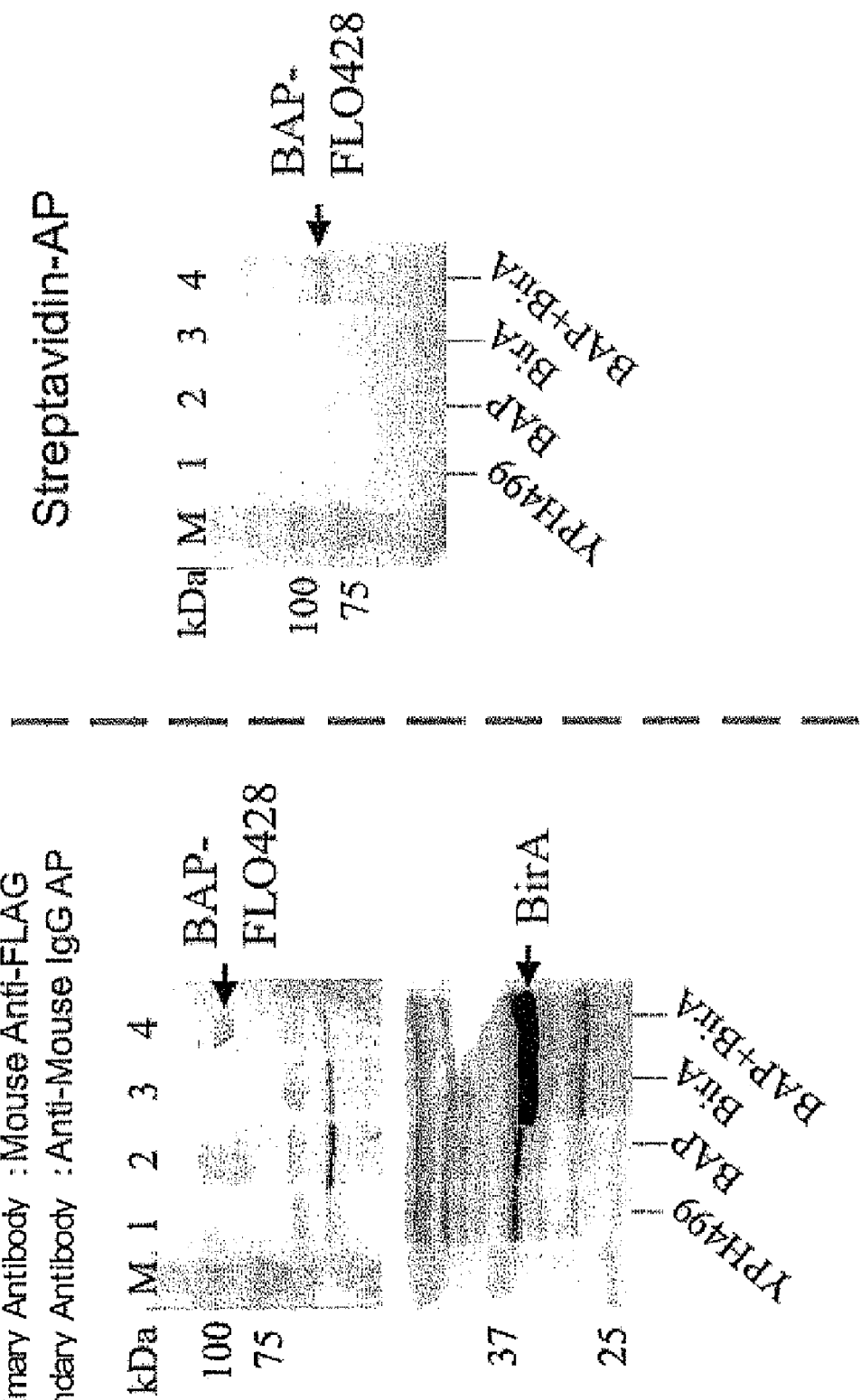
FIG. 2 shows electrophoresis photographs of western blottings for the expressions of BirA and BAP (at the left hand) and the biotinylation of BAP by BirA (at the right hand) in the transformed yeasts.

Expressions of BirA and BAP and Biotinylation of BAP by BirA in Transformed Yeast First, cells from 5 ml of transformed yeast culture were disrupted by ultrasonication. The resultant supernatant was centrifuged at 1000×g at 25° C. for 5 minutes, to yield the whole cell protein fraction. The whole cell protein fraction was subjected to Western blotting with mouse anti-FLAG IgG antibody (obtained from Sigma) as a primary antibody and alkaline phosphatase (AP) labeled anti-mouse IgG antibody (obtained from Promega) as a secondary antibody to analyse the expressions of BirA and BAP. The results are shown in the electrophoresis photograph at the left hand of FIG. 2. In this electrophoresis photograph, Lanes 1, 2, 3 and 4 indicate the results for the untransformed yeast ("YPH499"), for the transformed yeast ("BAP") of Comparative Example 2, the transformed yeast ("BirA") of Comparative Example 1, and for the transformed yeast ("BAP+BirA") of Example 1, respectively M represents the molecular weight marker. The expressions of BirA and BAP were determined based on the appearance of bands for BAP-FL0428 between 100 kDa and 75 kDa and for BirA at 37 kDa. Accordingly, it could be confirmed that the transformed yeast ("BAP+BirA") of Example 1 expressed BirA and BAP.

Furthermore, Western blotting was performed in the same manner as above, except that AP labeled streptavidin (obtained from Promega) was used as an antibody. In this blotting, the presence of a protein bound to streptavidin was verified. The results are shown in the electrophoresis photograph at the right hand of FIG. 2. Also in this electrophoresis photograph, Lanes 1, 2, 3 and 4 indicate the results for the untransformed yeast ("YPH499"), for the transformed yeast ("BAP") of Comparative Example 2, the transformed yeast ("BirA") of Comparative Example 1, and for the transformed yeast ("BAP+BirA") of Example 1, respectively. Only for the transformed yeast ("BAP+BirA") of Example 1, did a band for BAP-FL0428 appear between 100 kDa and 75 kDa. This fact demonstrates that the expressed BAP was biotinylated by the expressed BirA in the transformed yeast of Example 1.

Example 3

Display of Biotin on the Surface of Transformed Yeast

Transformed yeasts were incubated in 3 ml of YPDA medium (yeast extract-peptone-dextrose-adenine medium) at 30° C. for 18 hours, and 15 μl of yeast culture was collected and washed. To the yeast culture, streptavidin—fluorescein isocyanate (FITC) (obtained from Sigma) was then added to a final concentration of 20 μg/ml, and allowed to stand for 1 hour. After washing, the cells were observed by microscopy.

Figure 3:
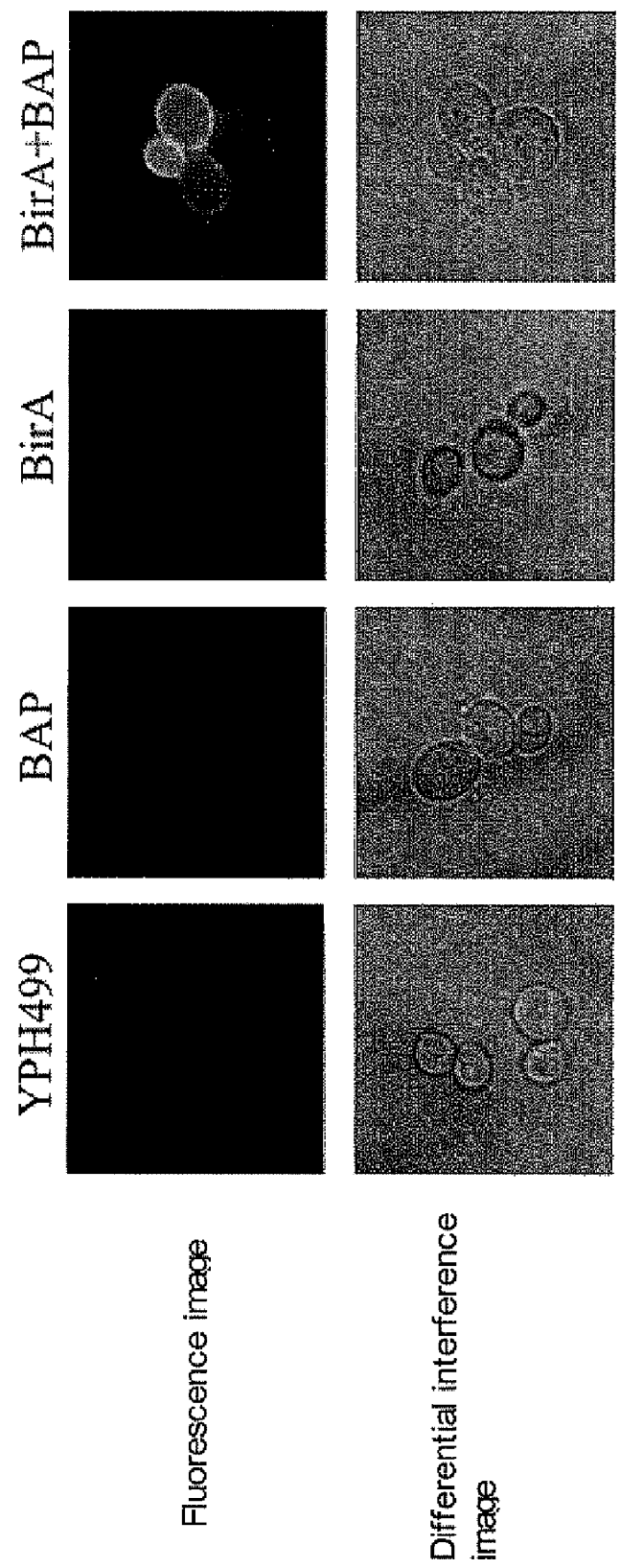
FIG. 3 shows fluorescence photomicrographs (at the line of "Fluorescence image") and differential interference photomicrographs (at the line of "Differential interference image") of the transformed yeasts to which streptavidin-FITC was added.

FIG. 3 shows fluorescence photomicrographs (at the line of "fluorescence image") and differential interference photomicrographs (at the line of "differential interference image") of the transformed yeasts to which streptavidin—FITC was added. The photomicrographs respectively show the results for the untransformed yeast ("YPH499"), the transformed yeast ("BAP") of Comparative Example 2, the transformed yeast ("BirA") of Comparative Example 1, and the transformed yeast ("BAP+BirA") of Example 1. When biotin was displayed on the cell surface of the yeast, the added streptavidin was bound and fluorescence was observed due to FITC which had been bound to the streptavidin. Fluorescence due to FITC was observed on the cell surface of the transformed yeast ("BAP+BirA") of Example 1. Accordingly, it was found that streptavidin was bound to the transformed yeast of Example 1.

Thus, it was demonstrated that biotin was displayed on the surface of the transformed yeast of Example 1.

Example 4

Display of Intended Molecule on Cell Surface Using Transformed Yeast and Streptavidin-Biotin Interaction Transformed yeasts were cultured in 3 ml of YPDA medium at 30° C. for 18 hours, and 15 μl of yeast culture was collected and washed. To the yeast culture, streptavidin was then added to a final concentration of 20 μg/ml, and allowed to stand for 1 hour, and then washed. Furthermore, biotin-FITC (obtained from PIERCE) was added to a final concentration of 0.01 μg/ml, and allowed to stand for 1 hour. After washing, the cells were observed by microscopy.

Figure 4:
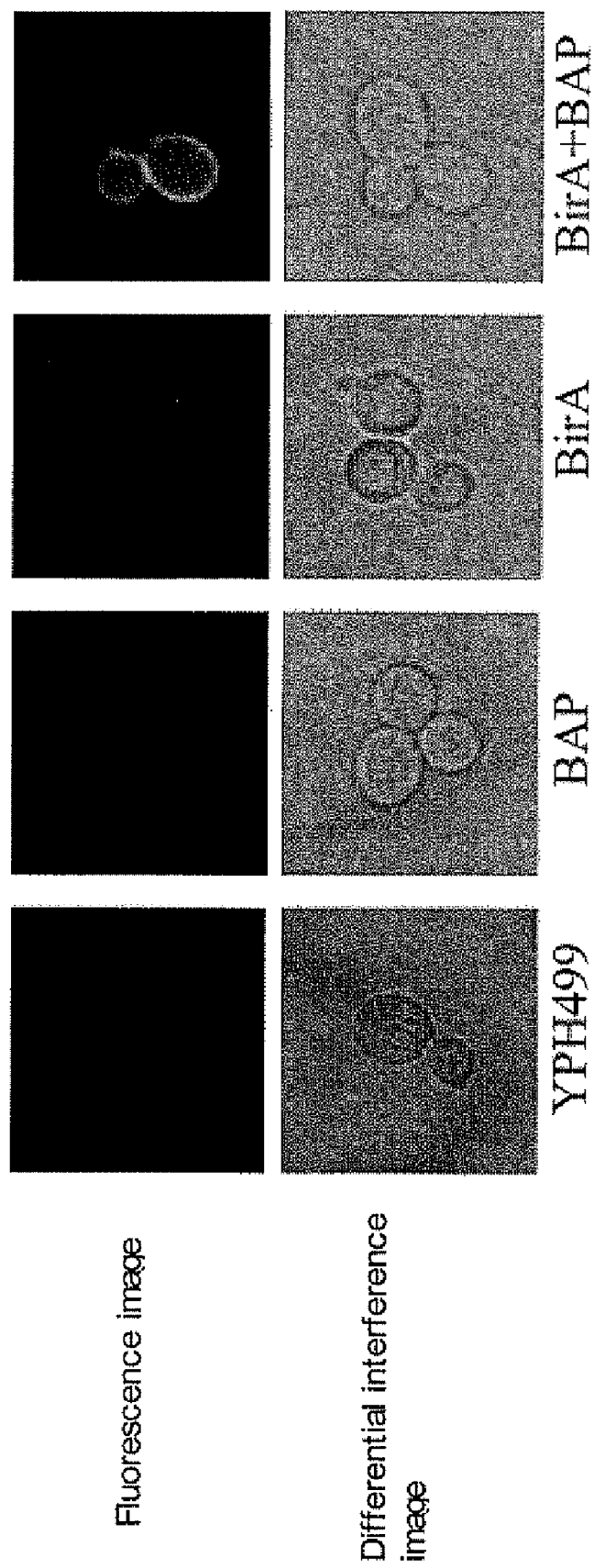
FIG. 4 shows fluorescence photomicrographs (at the line of "Fluorescence image") and differential interference photomicrographs (at the line of "Differential interference image") of the transformed yeasts to which streptavidin and biotin-FITC were added.

FIG. 4 shows fluorescence photomicrographs (at the line of "fluorescence image") and differential interference photomicrographs (at the line of "differential interference image") of the transformed yeasts to which streptavidin and biotin-FITC were added. The photomicrographs respectively show the results for the untransformed yeast ("YPH499"), the transformed yeast ("BAP") of Comparative Example 2, the transformed yeast ("BirA") of Comparative Example 1, and the transformed yeast ("BAP+BirA") of Example 1. Fluorescence due to FITC was observed on the cell surface of the transformed yeast ("BAP+BirA") of Example 1. Accordingly, it was found that streptavidin and then biotin were sequentially bound to the transformed yeast of Example 1.

Thus, it was demonstrated that to biotin displayed on the surface of the transformed yeast of Example 1, streptavidin and then biotin were sequentially bound, and FITC bound by the bound biotin was displayed on the surface.

Example 5

Production of *Escherichia Coli* that Displays Biotin on the Surface

A vector pHLA for surface display and the linkage product of BAP encoding gene and FLAG gene, which had been prepared as in Example 1, were digested with both of BamHl and HindIII, respectively, followed by ligation. The resultant vector contained the HCE promoter, PgsA gene segment, and the linkage product of BAP encoding gene and FLAG encoding segment. This vector was used to transform *E. coli* nov-ablue using electroporation. The resultant cells were incubated for 24 hours, and washed three times with 1 ml of phosphate buffered saline (PBS), and then suspended in 300 μl of PBS, and to this, anti-FLAG-FITC (obtained from Sigma) was added to a concentration of approximately 5 μg/ml, or alternatively, streptavidin-FITC was added to a concentration of approximately 5 μg/ml, followed by shaken for 30 minutes. Then, after washing with PBS, the cells were analyzed by fluorescence activated cell sorting (FACS) to verify the presences of FLAG and biotin on the cell surface. For the sake of comparison, untransformed *E. coli* was used.

Figure 5:
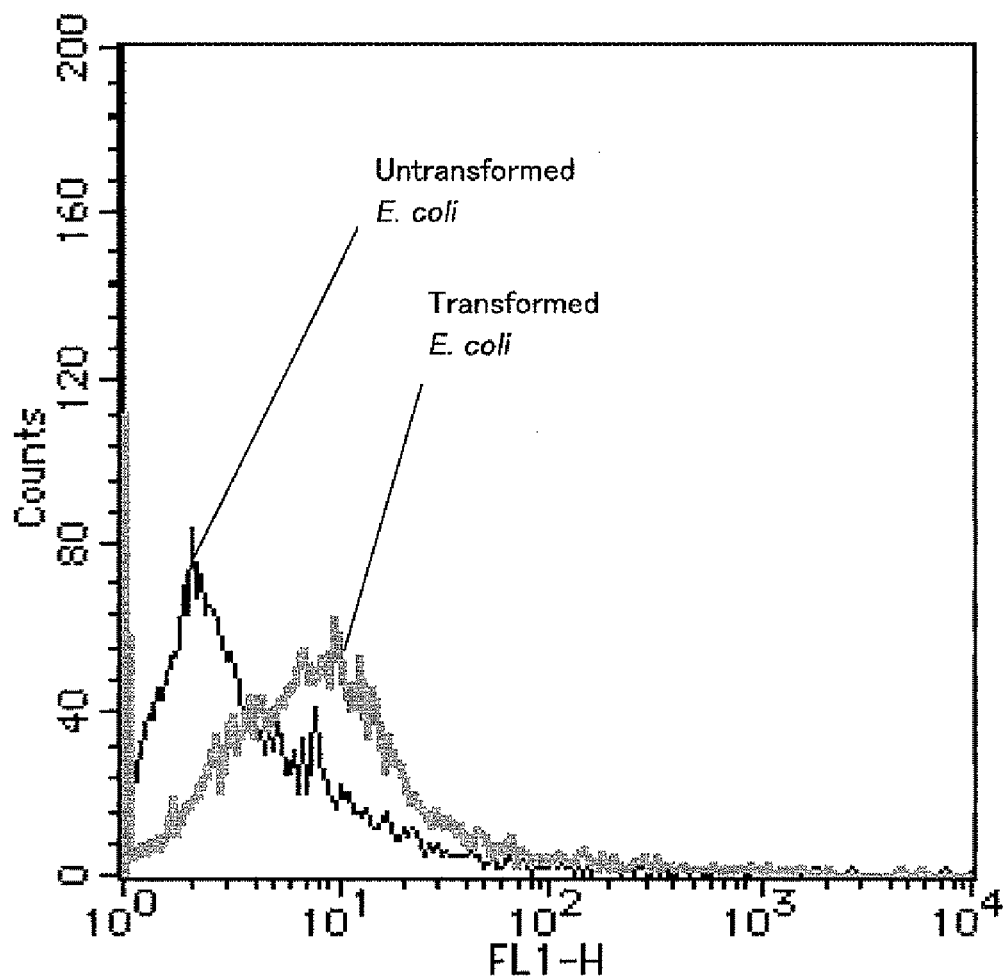
FIG. 5 is a graph showing the fluorescence intensities of transformed *E. coli* and untransformed *E. coli* analyzed by FACS, with anti-FLAG-FITC.

FIG. 5 is a graph showing the fluorescence intensities of transformed *E. coli* and untransformed *E. coli* analyzed by FACS, with anti-FLAG-FITC. In this graph, the horizontal axis represents the fluorescence intensity, and the vertical axis represents the number of cells (counts). It was observed that the fluorescence intensity of the transformed *E. coli* was stronger than that of the untransformed *E. coli*. Accordingly, it was demonstrated that FLAG was displayed on the cell surface of the transformed *E. coli*.

Figure 6:
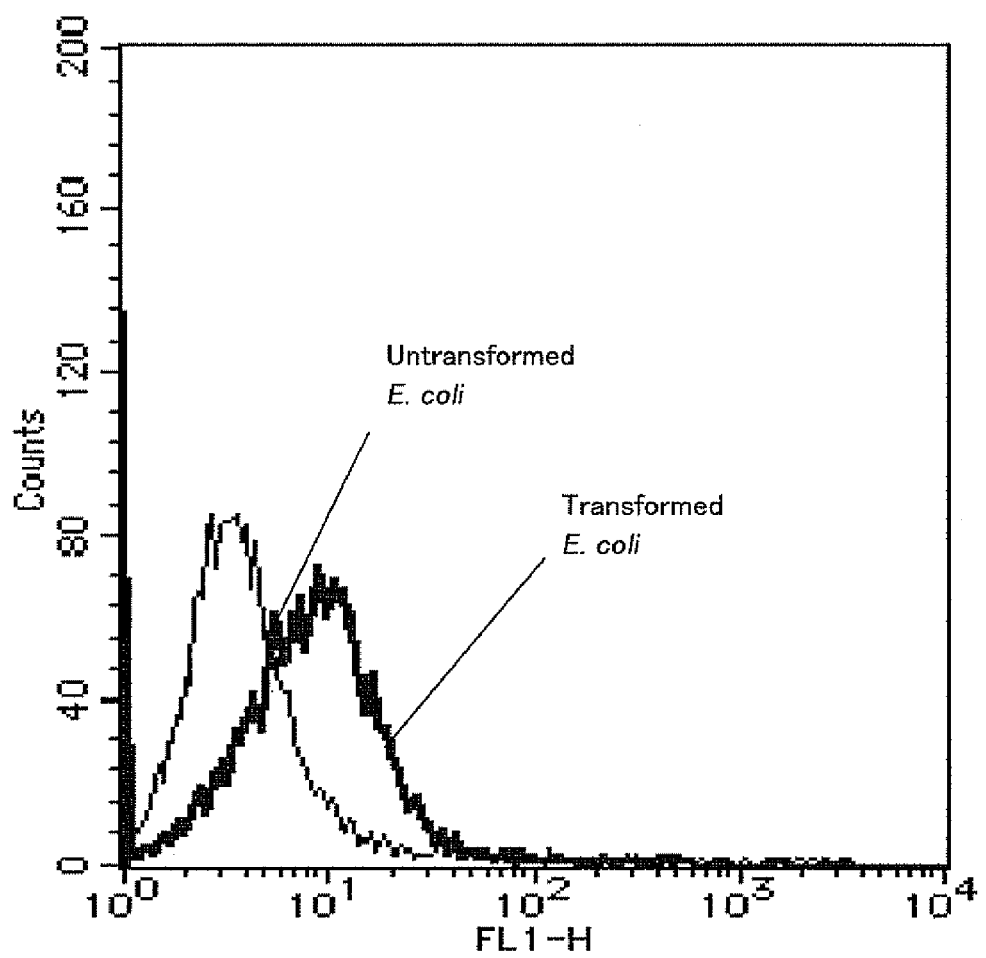
FIG. 6 is a graph showing the fluorescence intensiies of transformed *E. coli* and untransformed *E. coli* analyzed by FACS, with streptavidin-FITC.

FIG. 6 is a graph showing the fluorescence intensities of transformed *E. coli* and untransformed *E. coli* analyzed by FACS, with streptavidin-FITC. The horizontal axis and the vertical axis are as described for FIG. 5. It was observed that the fluorescence intensity of the transformed *E. coli* was stronger than that of the untransformed *E. coli*. Accordingly, it was shown that biotin was displayed on the cell surface of the transformed *E. coli*.

*E coli* that displayed biotin on the surface was obtained in the above-described manner.

According to the present invention, fluorescent molecules or environment-responsible, non-natural molecules can be displayed for the application as a biosensor. Also, non-natural molecules such as ligands with a strong affinity to heavy metals can be displayed for the application in the environmental purification and rare metal recovery. Also, non-proteineous catalysts can be displayed for the application as cellular catalysts.

What is claimed is:

1. A method for displaying an intended molecule on a cell surface of a microorganism, comprising
    reacting a microorganism with a streptavidin or an avidin, wherein the microorganism expresses a biotin ligase which biotinylates a lysine of an acceptor peptide to display a first biotin on the cell surface; and
    reacting a second biotin with the streptavidin or avidin, wherein the second biotin is bound to an intended molecule.

2. A method for producing a microorganism that displays an intended molecule on a cell surface, comprising
    reacting a microorganism with a streptavidin or an avidin, wherein the microorganism expresses a biotin ligase which biotinylates a lysine of an acceptor peptide to display a first biotin on the cell surface; and
    reacting a second biotin with the streptavidin or avidin, wherein the second biotin is bound to an intended molecule.

3. A recombinant microorganism that displays an intended molecule on a cell surface obtained according to the method of claim 2.

4. The method of claim 1, wherein the biotin ligase is *Escherichia coli* biotin ligase, and the sequence recognized by the *Escherichia coli* biotin ligase is the amino acid sequence GLNDIFEAQKIEWHE of SEQ ID NO: 1.

5. The method of claim 1, wherein the microorganism is a yeast or *Escherichia coli*.

6. The method of claim 2, wherein the biotin ligase is *Escherichia coli* biotin ligase, and the sequence recognized by the *Escherichia coli* biotin ligase is the amino acid sequence GLNDIFEAQKIEWHE of SEQ ID NO: 1.

7. The method of claim 2, wherein the microorganism is a yeast or *Escherichia coli*.

8. The method of claim 4, wherein the microorganism is a yeast or *Escherichia coli*.

9. The method of claim 6, wherein the microorganism is a yeast or *Escherichia coli*.

10. The method of claim 1, wherein the first biotin is bound to the steptavidin or the avidin, which is further bound to the second biotin.

11. The method of claim 2, wherein the first biotin is bound to the steptavidin or the avidin, which is further bound to the second biotin.

* * * * *

UNITED STATES PATENT AND TRADEMARK OFFICE
CERTIFICATE OF CORRECTION

PATENT NO.       : 8,252,577 B2
APPLICATION NO.  : 12/431102
DATED            : August 28, 2012
INVENTOR(S)      : Akihiko Kondo et al.

It is certified that error appears in the above-identified patent and that said Letters Patent is hereby corrected as shown below:

Column 16, Line 35, Claim 6, delete "of" and insert -- according to --

Column 16, Line 39, Claim 7, delete "of" and insert -- according to --

Column 16, Line 46, Claim 10, delete "steptavidin" and insert -- streptavidin --

Column 16, Line 49, Claim 11, delete "steptavidin" and insert -- streptavidin --

Signed and Sealed this
Fourth Day of December, 2012

David J. Kappos
*Director of the United States Patent and Trademark Office*

SEQUENCE LISTING

```
<160> NUMBER OF SEQ ID NOS: 5

<210> SEQ ID NO 1
<211> LENGTH: 15
<212> TYPE: PRT
<213> ORGANISM: Artificial
<220> FEATURE:
<223> OTHER INFORMATION: Biotin recognition sequence

<400> SEQUENCE: 1

Gly Leu Asn Asp Ile Phe Glu Ala Gln Lys Ile Glu Trp His Glu
1               5                   10                  15

<210> SEQ ID NO 2
<211> LENGTH: 45
<212> TYPE: DNA
<213> ORGANISM: Artificial
<220> FEATURE:
<223> OTHER INFORMATION: BirA forward primer

<400> SEQUENCE: 2
gcgctagccg gatccccgg gatgaaggat aacaccgtgc cactg                45

<210> SEQ ID NO 3
<211> LENGTH: 67
<212> TYPE: DNA
<213> ORGANISM: Artificial
<220> FEATURE:
<223> OTHER INFORMATION: BirA reverse primer

<400> SEQUENCE: 3
cgagatcttt acttatcgtc atccttgtaa tcgaattctt tttctgcact acgcagggat    60
```

```
atttcac                                                              67

<210> SEQ ID NO 4
<211> LENGTH: 77
<212> TYPE: DNA
<213> ORGANISM: Artificial
<220> FEATURE:
<223> OTHER INFORMATION: pFGK426-BAP forward primer

<400> SEQUENCE: 4
gcgtcgacgc atatccatat gatgttccag attatgctgg atccggcggc ctgaacgaca    60
tcttcgaggc ccagaag                                                   77

<210> SEQ ID NO 5
<211> LENGTH: 77
<212> TYPE: DNA
<213> ORGANISM: Artificial
<220> FEATURE:
<223> OTHER INFORMATION: pFGK426-BAP reverse primer

<400> SEQUENCE: 5
ccgctttaat taacttatcg tcgtcatcct tgtaatctgc gaattcctcg tgccactcga    60
tcttctgggc ctcgaag                                                   77
```